Feb. 19, 1974 L. H. SHOESMITH Plant Pat. 3,484
CHRYSANTHEMUM PLANT (SILVER COIN)
Filed Aug. 10, 1972
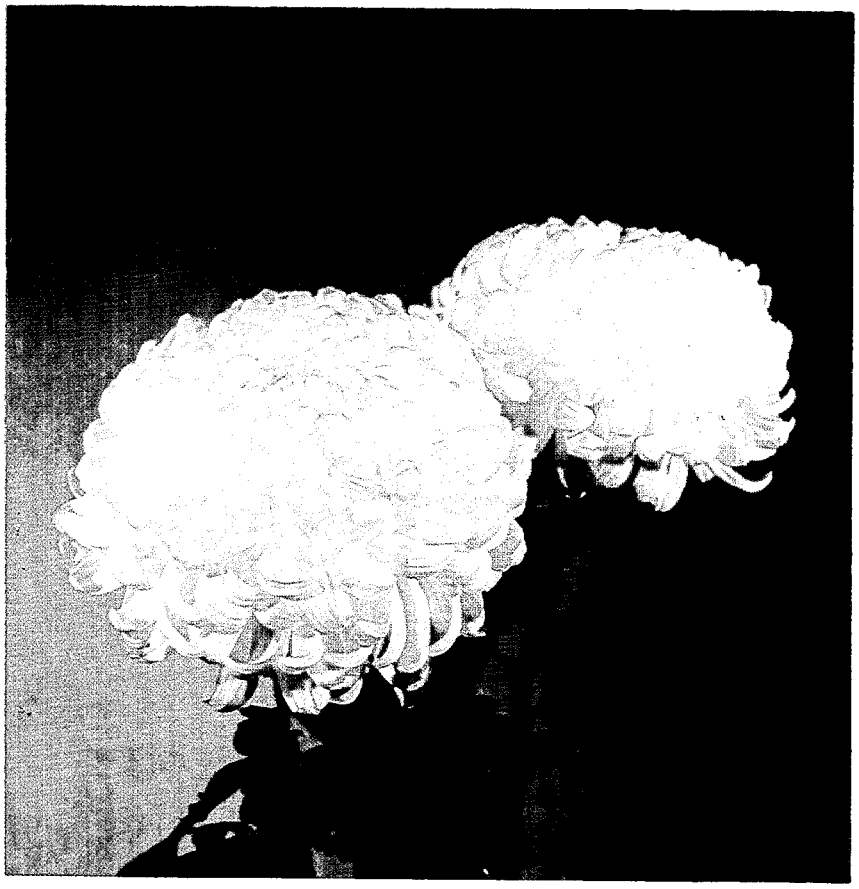
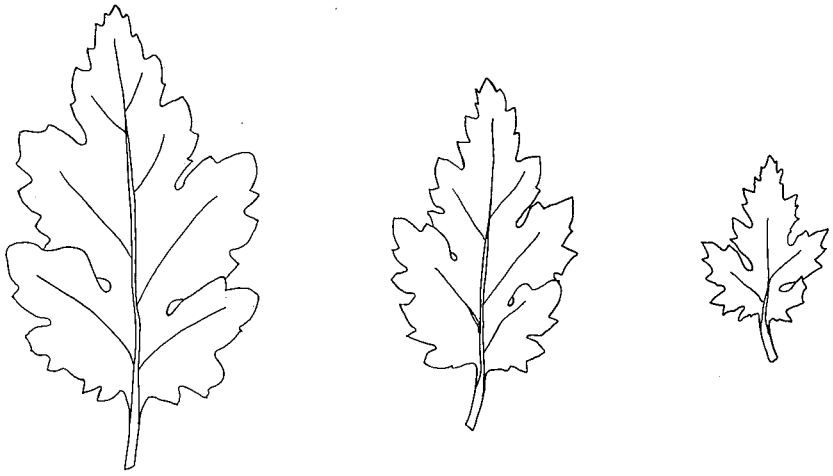

United States Patent Office

Plant Pat. 3,484
Patented Feb. 19, 1974

3,484

CHRYSANTHEMUM PLANT

Leonard H. Shoesmith, Westfield-Woking, England, assignor to Pan-American Plant Company, Chicago, Ill.

Filed Aug. 10, 1972, Ser. No. 279,511
Int. Cl. A01h *5/00*
U.S. Cl. Plt.—77 1 Claim

ABSTRACT OF THE DISCLOSURE

A new variety of *Chrysanthemum morifolium* of standard type for greenhouse culture, having a ten-week response to photoperiod culture and being particularly adapted for fall, winter and spring flowering. This plant is a vigorous grower producing abundant foliage and very large pure white flowers.

BACKGROUND OF THE NEW PLANT

My new variety of white chrysanthemum plant originated as a seedling of unknown parentage and was found by me among a group of greenhouse plants being grown for use in an extensive breeding program being carried on with the object of developing improved chrysanthemum varieties for commercial trade. This plant came to my attention in November 1968 because of its very large pure white flowers and its apparently vigorous growth habit. Asexual propagation of this plant, by means of cuttings from the original plant, under my direction at West Chicago, Ill., and subsequent thorough testing of the plants so produced has demonstrated that this new variety possesses valuable characteristics of habit and flowering ability in addition to its outstanding blossoms. Further propagation of this new variety, by means of vegetative cuttings, at West Chicago, Ill., and at Cortez, Fla., has shown the distinctive characteristics of this plant to be firmly fixed and to hold true from generation to generation.

DESCRIPTION OF THE DRAWING

This new variety of chrysanthemum plant is illustrated by the accompanying drawing which shows form and color of the flower by photographic procedure and the configuration of typical specimens of the leaves by pen and ink drawings.

DESCRIPTION OF THE NEW PLANT

The following is a detailed description of the new variety of chrystanthemum plant with color designations according to Robert F. Wilson's Horticultural Colour Chart issued by The British Colour Council.

*The plant*

Origin: Seedling
Parentage: Unknown, this seedling having been selected from among many resulting from random crosses
Classification: *Botanic—Chrysanthemum morifolium*
*Commercial.*—White, 10-week standard
Form: Perennial herbaceous bush
Height: Grows naturally to about 3 feet
Growth: Terminal. Vigorous, study and upright with good strength
Branching: Under natural conditions, branching occurs
Foliage: Abundant, producing 27 leaves on a 3-foot stem
*Leaf size.*—Mature leaf—5½ inches long x 3 inches wide

*Shape.*—Lanceolate and pinnately lobed, slightly serrated
*Surface texture.*—Glaucous
*Color.*—Upper side—Spinach Green 0960/1. Under side—Spinach Green 0960/2
*Venation.*—Pinnate
*Petioles.*—⅞ inch long

*The bud*

Form: Globular
Size: ⅝ inch diameter x ⅝ inch depth when phyllaries begin to separate
Opening: Slowly. The phyllaries begin to divide about two weeks after bud becomes visible. Flowering occurs about four weeks later.
Color:
*When phyllaries first divide.*—Lettuce Green 861
*When florets begin to unfurl.*—Lettuce Green 861
Phyllaries: The outside of the receptacle bears many distinct involucral bracts which are spear shaped and stand up.
*Color.*—Inside—Spinach Green 0960/2. Outside—Spinach Green 0960/3
*Surface Aspect.*—Canescent
Calyx: Represented by tiny bristles arising from the top of the ovary. Ofter absent
*Length.*—½ inch
*Surface aspect.*—Canescent

*The flower*

Response: 10-week
Recommended flowering: Fall, winter and spring. Can be flowered the year around with photoperiod control.
Natural season flowering: Late October
Blooms: Flower type—standard incurve
*Borne.*—A head of many florets borne on a receptacle
*Size.*—Very large, 5 to 6 inches in diameter and 4 inches in depth
*Shape.*—Flat and round when first opening, becoming globular as florets develop
*Florets.*—Very many in number. Form. Linear Color Outer floret.—Pure White with base of Pod Green 061; inside floret.—Pure White; reverse sides of florets.—Pure White. Firmness: Soft. Appearance: Satiny. Discoloration: None
*Peduncle.*—Sturdy—¼ inch long. Color: Scheeles Green 860/1
Persistence: Florets hang on and dry
Effect of weather: During hot and high light periods of the year, the petals become very firm and leathery. The best plants and flowers are produced in the fall, winter and spring.
Lasting quality:
*On plant.*—Approximately 3 weeks
As cut flowers.—About 2 weeks

*Reproductive organs*

Stamens:
*Filaments.*—5, syngeneiously arranged. Length: ¼ inch. Color: Light Yellow
*Anthers.*—Connate
*Pollen.*—Color—Yellow
Pistils: Number—one for each ray floret
*Style.*—Length—5/16 inch
*Stigmas.*—Color—Straw Yellow
Ovaries: Inferior, bicarpellate and sterile.

This new variety of chrysanthemum probably most nearly resembles May Shoesmith (unpatented) in flower form but flowers from ten days to two weeks earlier and with more open blooms having fewer and not as tightly incurved florets. Grown as a standard variety this plant produces large pure white flowers and is most excellent for winter-time flowering, keeping a well developed flower form in the long, cloudy periods of the northern U.S. areas.

I claim:

1. A new and distinct variety of chrysanthemum plant, substantially as herein shown and described, characterized by its very large pure white blooms, its excellent growth and production for wintertime flowering, and its ability to keep a well developed flower form in the long cloudy periods of the northern U.S. winter months.

No references cited.

ROBERT E. BAGWILL, Primary Examiner